(12) United States Patent
Wasserman

(10) Patent No.: US 12,201,831 B2
(45) Date of Patent: Jan. 21, 2025

(54) IMPEDANCE TOMOGRAPHY USING ELECTRODES OF A TUMOR TREATING FIELDS (TTFIELDS) SYSTEM

(71) Applicant: Novocure GmbH, Root (CH)

(72) Inventor: Yoram Wasserman, Haifa (IL)

(73) Assignee: Novocure GmbH, Root (CH)

( * ) Notice: Subject to any disclaimer, the term of this patent is extended or adjusted under 35 U.S.C. 154(b) by 475 days.

(21) Appl. No.: 17/710,041

(22) Filed: Mar. 31, 2022

(65) Prior Publication Data

US 2022/0313992 A1  Oct. 6, 2022

Related U.S. Application Data

(60) Provisional application No. 63/169,098, filed on Mar. 31, 2021.

(51) Int. Cl.
*A61N 1/36* (2006.01)
*A61B 5/053* (2021.01)
(Continued)

(52) U.S. Cl.
CPC .......... *A61N 1/36002* (2017.08); *A61B 5/053* (2013.01); *A61N 1/0476* (2013.01);
(Continued)

(58) Field of Classification Search
CPC ... A61N 1/00; A61N 1/02; A61N 1/10; A61N 1/18; A61N 1/20; A61N 1/32; A61N 1/40;
(Continued)

(56) References Cited

U.S. PATENT DOCUMENTS

| 5,233,987 A | 8/1993 | Fabian et al. |
| 6,868,289 B2 | 3/2005 | Palti |

(Continued)

FOREIGN PATENT DOCUMENTS

| WO | 2014181167 A1 | 11/2014 |
| WO | 2017072706 A1 | 5/2017 |

(Continued)

OTHER PUBLICATIONS

International Search Report and Written Opinion issued in application No. PCT/IB2022/053038 dated Jun. 22, 2022.

(Continued)

*Primary Examiner* — Don K Wong
(74) *Attorney, Agent, or Firm* — Potomac Law Group, PLLC

(57) ABSTRACT

Treatment of a target region using alternating electric fields (e.g., TTFields) may be planned by determining, based on a plurality of impedance measurements obtained during a first window of time, a first impedance at each of a plurality of voxels that correspond to the target region. Then, based on the first impedances, a plan for treating the target region with alternating electric fields is generated. Subsequently, an electric field may be induced in the target region based on the plan. In some embodiments, a baseline MRI of the target region is obtained, and contemporaneous baseline impedances are registered to the MRI. In these embodiments, the plan for treating the target region is further based on a comparison between the first impedances and the baseline impedances.

20 Claims, 8 Drawing Sheets

(51) Int. Cl.
*A61N 1/04* (2006.01)
*G01R 33/48* (2006.01)
*G16H 30/40* (2018.01)
*A61B 5/00* (2006.01)
*A61B 5/055* (2006.01)
*A61N 1/40* (2006.01)

(52) U.S. Cl.
CPC ......... *G01R 33/4808* (2013.01); *G16H 30/40* (2018.01); *A61B 5/0042* (2013.01); *A61B 5/055* (2013.01); *A61B 2576/026* (2013.01); *A61N 1/40* (2013.01)

(58) Field of Classification Search
CPC .......... A61N 2/002; A61N 2/004; A61N 2/02; A61N 2/06; A61N 2/12; A61N 1/0476; A61N 5/10; A61N 1/327; A61N 1/0514; A61N 1/30617; A61N 1/36002; A61N 2007/003; A61B 5/0536; A61B 5/0537
See application file for complete search history.

(56) References Cited

U.S. PATENT DOCUMENTS

| | | | |
|---|---|---|---|
| 7,016,725 B2 | 3/2006 | Palti | |
| 7,089,054 B2 | 8/2006 | Palti | |
| 7,136,699 B2 | 11/2006 | Palti | |
| 7,333,852 B2 | 2/2008 | Palti | |
| 7,467,011 B2 | 12/2008 | Palti | |
| 7,519,420 B2 | 4/2009 | Palti | |
| 7,565,205 B2 | 7/2009 | Palti | |
| 7,565,208 B2 | 7/2009 | Palti | |
| 7,599,745 B2 | 10/2009 | Palti | |
| 7,599,746 B2 | 10/2009 | Palti | |
| 7,706,890 B2 | 4/2010 | Palti | |
| 7,715,921 B2 | 5/2010 | Palti | |
| 7,805,201 B2 | 9/2010 | Palti | |
| 7,890,183 B2 | 2/2011 | Palti et al. | |
| 7,912,540 B2 | 3/2011 | Palti | |
| 7,917,227 B2 | 3/2011 | Palti | |
| 8,019,414 B2 | 9/2011 | Palti | |
| 8,027,738 B2 | 9/2011 | Palti | |
| 8,170,884 B2 | 5/2012 | Palti | |
| 8,175,698 B2 | 5/2012 | Palti et al. | |
| 8,229,555 B2 | 7/2012 | Palti | |
| RE43,618 E | 8/2012 | Palti | |
| 8,244,345 B2 | 8/2012 | Palti | |
| 8,406,870 B2 | 3/2013 | Palti | |
| 8,447,395 B2 | 5/2013 | Palti et al. | |
| 8,447,396 B2 | 5/2013 | Palti et al. | |
| 8,465,533 B2 | 6/2013 | Palti | |
| 8,706,261 B2 | 4/2014 | Palti | |
| 8,715,203 B2 | 5/2014 | Palti | |
| 8,718,756 B2 | 5/2014 | Palti | |
| 8,753,381 B2 | 6/2014 | Henriksson et al. | |
| 8,764,675 B2 | 7/2014 | Palti | |
| 9,023,090 B2 | 5/2015 | Palti | |
| 9,023,091 B2 | 5/2015 | Palti | |
| 9,039,674 B2 | 5/2015 | Palti et al. | |
| 9,056,203 B2 | 6/2015 | Palti et al. | |
| 9,440,068 B2 | 9/2016 | Palti et al. | |
| 9,655,669 B2 | 5/2017 | Palti et al. | |
| 9,750,934 B2 | 9/2017 | Palti et al. | |
| 9,910,453 B2 | 3/2018 | Wasserman et al. | |
| 10,188,851 B2 | 1/2019 | Wenger et al. | |
| 10,441,776 B2 | 10/2019 | Kirson et al. | |
| 10,779,875 B2 | 9/2020 | Palti et al. | |
| 11,191,956 B2 | 12/2021 | Giladi et al. | |
| 2006/0167499 A1 | 7/2006 | Palti | |
| 2007/0225766 A1 | 9/2007 | Palti | |
| 2007/0239213 A1 | 10/2007 | Palti | |
| 2009/0076366 A1 | 3/2009 | Palti | |
| 2012/0283726 A1 | 11/2012 | Palti | |
| 2014/0330268 A1 | 11/2014 | Palti et al. | |
| 2017/0120041 A1 | 5/2017 | Wenger et al. | |
| 2017/0215939 A1 | 8/2017 | Palti et al. | |
| 2017/0281934 A1 | 10/2017 | Giladi et al. | |
| 2018/0001075 A1 | 1/2018 | Kirson et al. | |
| 2018/0008708 A1 | 1/2018 | Giladi et al. | |
| 2018/0050200 A1 | 2/2018 | Wasserman et al. | |
| 2018/0160933 A1 | 6/2018 | Urman et al. | |
| 2018/0202991 A1 | 7/2018 | Giladi et al. | |
| 2018/0280687 A1 | 10/2018 | Carter et al. | |
| 2019/0117956 A1 | 4/2019 | Wenger et al. | |
| 2019/0117963 A1 | 4/2019 | Travers et al. | |
| 2019/0307781 A1 | 10/2019 | Krex et al. | |
| 2019/0308016 A1* | 10/2019 | Wenger | G01R 33/5608 |
| 2020/0001069 A1 | 1/2020 | Kirson et al. | |
| 2020/0009376 A1 | 1/2020 | Chang et al. | |
| 2020/0009377 A1 | 1/2020 | Chang et al. | |
| 2020/0016067 A1 | 1/2020 | Gotlib et al. | |
| 2020/0022650 A1 | 1/2020 | Varkuti | |
| 2020/0023179 A1 | 1/2020 | Bomzon et al. | |
| 2020/0061360 A1 | 2/2020 | Hagemann et al. | |
| 2020/0061361 A1 | 2/2020 | Hagemann et al. | |
| 2020/0069937 A1 | 3/2020 | Naveh et al. | |
| 2020/0078582 A1 | 3/2020 | Alon et al. | |
| 2020/0108031 A1 | 4/2020 | Borst et al. | |
| 2020/0114141 A1 | 4/2020 | Bomzon et al. | |
| 2020/0121728 A1 | 4/2020 | Wardak et al. | |
| 2020/0129761 A1 | 4/2020 | Bomzon et al. | |
| 2020/0146586 A1 | 5/2020 | Naveh et al. | |
| 2020/0155835 A1 | 5/2020 | Wasserman et al. | |
| 2020/0171297 A1 | 6/2020 | Kirson et al. | |
| 2020/0179512 A1 | 6/2020 | Giladi et al. | |
| 2020/0219261 A1 | 7/2020 | Shamir et al. | |
| 2020/0269037 A1 | 8/2020 | Hagemann et al. | |
| 2020/0269041 A1 | 8/2020 | Zeevi et al. | |
| 2020/0368525 A1 | 11/2020 | Maag et al. | |
| 2021/0031031 A1 | 2/2021 | Wasserman et al. | |
| 2021/0038584 A1 | 2/2021 | Voloshin-Sela | |
| 2021/0060334 A1 | 3/2021 | Avraham et al. | |
| 2021/0069503 A1 | 3/2021 | Tran et al. | |
| 2021/0187277 A1 | 6/2021 | Wasserman et al. | |
| 2021/0196348 A1 | 7/2021 | Wasserman | |
| 2021/0199640 A1 | 7/2021 | Patel et al. | |
| 2021/0203250 A1 | 7/2021 | Wasserman | |
| 2021/0268247 A1 | 9/2021 | Story et al. | |
| 2021/0299440 A1 | 9/2021 | Deslauriers et al. | |
| 2021/0308446 A1 | 10/2021 | Alon et al. | |
| 2021/0330950 A1 | 10/2021 | Hagemann et al. | |
| 2021/0346694 A1 | 11/2021 | Wasserman et al. | |
| 2021/0379362 A1 | 12/2021 | Smith et al. | |
| 2021/0408383 A1 | 12/2021 | Kalra et al. | |
| 2022/0095997 A1 | 3/2022 | Wasserman | |
| 2022/0096821 A1 | 3/2022 | Kirson et al. | |
| 2022/0118249 A1 | 4/2022 | Bomzon et al. | |
| 2022/0161028 A1 | 5/2022 | Giladi et al. | |
| 2022/0193435 A1 | 6/2022 | Wasserman et al. | |

FOREIGN PATENT DOCUMENTS

| | | |
|---|---|---|
| WO | 2021038416 A1 | 3/2021 |
| WO | 2021137094 A1 | 7/2021 |

OTHER PUBLICATIONS

Li et al., "Evaluating the therapeutic effect of tumor treating fields (TTFields) by monitoring the impedance across 2 TTFields electrode arrays," PeerJ, vol. 10, p. 12877, Feb. 2022.

* cited by examiner

IMPEDANCE TOMOGRAPHY USING ELECTRODES OF A TUMOR TREATING FIELDS (TTFIELDS) SYSTEM

CROSS REFERENCE TO RELATED APPLICATIONS

This Application claims the benefit of U.S. Provisional Application 63/169,098, filed Mar. 31, 2021, which is incorporated herein by reference in its entirety.

BACKGROUND

Tumor Treating Fields (TTFields) are an effective anti-neoplastic treatment modality delivered via non-invasive application of low intensity, intermediate frequency (e.g., 100-500 kHz), alternating electric fields. The prior art Optune® system delivers TTFields to a tumor via two pairs of transducer arrays (each of which includes 9 or more electrode elements that are all wired in parallel) that are placed on the subject's skin in close proximity to the tumor. Typically, one pair of transducer arrays is positioned on the right and left sides of the tumor, and the other pair of transducer arrays is positioned anterior and posterior to the tumor. The transducer arrays are connected via cables to an AC signal generator. The AC signal generator (a) sends an AC current through the right/left pair of arrays during a first period of time, which induces an electric field with a first direction through the tumor; then (b) sends an AC current through the anterior/posterior pair of arrays during a second period of time, which induces an electric field with a second direction through the tumor; then repeats steps (a) and (b) for the duration of the treatment.

The efficacy of TTFields treatment depends on the field intensity (or power density) of the electric field that is delivered to the tumor. Some experiments have shown, for example, that TTFields are more effective when the field intensity is at least 1 V/cm.

The traditional approach for estimating the field intensity (or power density) that is delivered to the tumor relies on numeric simulation techniques that (a) generate a model of the electrical characteristics of the relevant body part from an MRI, (b) position model electrodes on the model body part, and (c) calculate what the intensity of the electric field will be within the tumor when a given AC voltage is applied to the model electrodes. Although this technique can be very useful for determining where to position the arrays on the subject's body and what voltages must be applied in order to achieve the desired field intensity, the technique relies on assumptions about the electrical characteristics (e.g., conductivity) of the tissue between the electrodes.

For example, in the case of a brain tumor, an MRI of the brain is obtained; the MRI is segmented into different types of tissue (e.g., white matter, gray matter, cerebrospinal fluid, etc.); a conductivity value obtained from the scientific literature is assigned to each type of tissue; and the assigned conductivities are used to make a 3D model of the brain, skull, and scalp. Model electrodes are then positioned on the 3-D model, and numeric simulation techniques are used to determine the field intensity within the tumor when a voltage is applied to the model electrodes. But because this technique uses conductivity values obtained from the literature for each type of tissue (instead of using the actual conductivity of each voxel for the specific subject who is about to receive treatment using TTFields), the technique can only provide an estimate of the field intensity or power density in the tumor.

SUMMARY OF THE INVENTION

Some aspects of the present application are directed to providing methods to determine an optimized electric field intensity and/or optimized positioning of electrode arrays on the body when applying TTFields to a subject.

One aspect of this application is directed to a first method of planning treatment of a target region in a subject's body using alternating electric fields. The first method comprises positioning a first set of N electrode elements on or in the subject's body on a first side of the target region, wherein N is at least 4; and positioning a second set of M electrode elements on or in the subject's body on a second side of the target region, wherein M is at least 4 and wherein the second side is opposite to the first side. The first method also comprises sequentially measuring, during a first window of time, a respective impedance or conductance between each of the N electrode elements in the first set and each of the M electrode elements in the second set; and calculating, based on the impedance or conductance measurements, a first impedance or conductance at each of at least 27 voxels that correspond to the target region. And the first method also comprises generating a plan, based on the first impedances or conductances of the voxels, for treating the target region with alternating electric fields.

Some instances of the first method further comprise positioning a third set of X electrode elements on or in the subject's body on a third side of the target region, wherein X is at least 4; positioning a fourth set of Y electrode elements on or in the subject's body on a fourth side of the target region, wherein Y is at least 4 and wherein the fourth side is opposite to the third side; and sequentially measuring, during the first window of time, a respective impedance or conductance between each of the X electrode elements in the third set and each of the Y electrode elements in the fourth set. The calculating of the first impedance or conductance at each of the at least 27 voxels is also based on the measured impedances or conductances between the electrode elements in the third set and the electrode elements in the fourth set.

Some instances of the first method further comprise, subsequent to the step of generating the plan, (a) applying an alternating voltage between a majority of the electrode elements in the first set and a majority of the electrode elements in the second set in order to induce an electric field in the target region, and (b) applying an alternating voltage between a majority of the electrode elements in the third set and a majority of the electrode elements in the fourth set in order to induce an electric field in the target region.

In some instances of the first method, the plan comprises generating a recommendation to move at least one set of electrode elements to a different position on or in the subject's body. Optionally, these instances may further comprise, prior to the step of generating the plan, (a) obtaining an MRI and (b) registering the voxels to the MRI, wherein the recommendation to move at least one set of electrode elements to a different position is also based on the MRI.

In some instances of the first method, N is at least 9, M is at least 9, X is at least 9, and Y is at least 9.

Some instances of the first method further comprise obtaining a baseline MRI of the target region at a baseline time that is prior to the first window of time; calculating, based on baseline impedance or conductance measurements obtained within 30 days of the baseline time, a baseline impedance or conductance at each of at least 27 voxels that correspond to the target region; and registering the baseline impedances or conductances of the voxels to the baseline MRI. The plan for treating the target region with alternating electric fields is further based on a comparison between the first impedances or conductances and the baseline impedances or conductances.

Another aspect of this application is directed to a second method of planning treatment of a target region in a subject's body using alternating electric fields. The second method comprises determining, based on a plurality of impedance or conductance measurements obtained during a first window of time, a first impedance or conductance at each of at least 27 voxels that correspond to the target region; and generating a plan for treating the target region with alternating electric fields, based on the first impedances or conductances of the voxels.

In some instances of the second method, the plurality of impedance or conductance measurements are obtained by positioning at least 10 electrode elements on or in the subject's body and applying a plurality of electrical signals to the electrode elements.

Some instances of the second method further comprise treating a tumor in the target region by applying an alternating voltage between a plurality of the electrode elements in order to induce an electric field in the target region.

Some instances of the second method further comprise obtaining a baseline MRI of the target region at a baseline time that is prior to the first window of time; calculating, based on baseline impedance or conductance measurements obtained within 30 days of the baseline time, a baseline impedance or conductance at each of at least 27 voxels that correspond to the target region; and registering the baseline impedances or conductances of the voxels to the baseline MRI. The plan for treating the target region with alternating electric fields is further based on a comparison between the first impedances or conductances and the baseline impedances or conductances.

Another aspect of this application is directed to a third method of adaptively treating a cancer patient by administering alternating electric fields to a target region in a patient's body combined with in-situ measurement of cancer progression or regression or redistribution in the target region. The third method comprises positioning a first set of N electrode elements on or in the patient's body on a first side of the target region, wherein N is at least 4; and positioning a second set of M electrode elements on or in the patient's body on a second side of the target region, wherein M is at least 4 and wherein the second side is opposite to the first side. The third method also comprises sequentially applying, during a first period of time, a plurality of electrical signals to the electrode elements in the first set and the electrode elements in the second set; and determining, based on the applied electrical signals, a first impedance or conductance at each of at least 27 voxels that correspond to the target region. The third method also comprises determining a first target location of at least one first target selected from the following cancer targets: tumor(s) or residual tumor(s), cancer cell cluster(s), cancer cell(s), or boundary region of cancer cells and healthy tissue. The third method also comprises delivering alternating electric fields treatment to the first target at the first target location in the patient's body; and monitoring changes over a second period of time in the electrical impedance or conductance of the voxels, using electrical impedance or conductance measurements, at least a portion of said second period of time includes time during which the patient is receiving alternating electric fields treatment. And the third method also comprises administering alternating electric fields to at least one second target in the target region, using a modified electric field intensity or a modified positioning, or both, for at least one set of electrode elements in response to observed changes in the electrical impedance or conductance of the voxels; and, optionally, repeating, one or more times, one or more steps.

Some instances of the third method further comprise positioning a third set of X electrode elements on or in the patient's body on a third side of the target region, wherein X is at least 4; positioning a fourth set of Y electrode elements on or in the patient's body on a fourth side of the target region, wherein Y is at least 4 and wherein the fourth side is opposite to the third side; and sequentially applying, during the first period of time, a plurality of electrical signals to the electrode elements in the third set and the electrode elements in the fourth set. The determining of the first impedance or conductance at each of the at least 27 voxels is also based on the plurality of electrical signals applied to the electrode elements in the third set and the electrode elements in the fourth set.

In some instances of the third method, the step of delivering alternating electric fields treatment to the first target at the first target location in the patient's body comprises (a) applying an alternating voltage between a majority of the electrode elements in the first set and a majority of the electrode elements in the second set in order to induce an electric field in the target region, and (b) applying an alternating voltage between a majority of the electrode elements in the third set and a majority of the electrode elements in the fourth set in order to induce an electric field in the target region.

In some instances of the third method, N is at least 9, M is at least 9, X is at least 9, and Y is at least 9.

Some instances of the third method further comprise, prior to the step of determining a first target location of at least one first target and prior to delivering alternating electric fields treatment to the first target, generating a baseline tomographic image of the target region based on the first impedance or conductance at each of the voxels that correspond to the target region. Optionally, these instances may further comprise, prior to the step of determining a first target location of at least one first target and prior to delivering alternating electric fields treatment to the first target, (a) obtaining a baseline MRI of the target region and (b) registering the first impedances or conductances at each of the voxels to the baseline MRI or registering the baseline tomographic image of the target region based on the first impedance or conductance at each of the voxels to the baseline MRI, wherein determining the first target location of the at least one first target is also based on the baseline MRI.

In some instances of the third method, monitoring changes over a second period of time in the electrical impedance or conductance of the voxels is used to assess progression or regression of cancer occurring at the first target location, or growth of a new cancer away from the first target location. In some instances of the third method, monitoring changes over a second period of time in the electrical impedance or conductance of the voxels, includes measuring electrical impedance or conductance of the voxels concurrently with administering alternating electric fields to the target region.

Some instances of the third method further comprise an iterative process of performing one or more steps of the method performed over a third period of time to identify one or more additional cancer targets at one or more new locations of growth of cancer away from the first target location and administering alternating electric fields to at least one of the additional cancer targets.

Some instances of the third method further comprise an iterative process of performing one or more steps of the method over a fourth period of time to predict a new location of growth of cancer away from the first target location and administering alternating electric fields to the new location.

Another aspect of this application is directed to a fourth method of planning treatment of a target region in a subject's body using alternating electric fields. The fourth method comprises positioning a first set of at least 4 electrode elements on or in the subject's body on a first side of the target region; and positioning a second set of at least 4 electrode elements on or in the subject's body on a second side of the target region, wherein the second side is opposite to the first side. The fourth method also comprises applying, during a first window of time, a first plurality of electrical signals to the electrode elements in the first set and the electrode elements in the second set; and determining a first plurality of electrical characteristics of the target region while the first plurality of electrical signals is being applied. And the fourth method also comprises generating a first tomographic image of the target region based on the determined first plurality of electrical characteristics; and generating a plan, based on the first tomographic image, for treating the target region with alternating electric fields.

Some instances of the fourth method further comprise, subsequent to the step of generating the plan, applying an alternating voltage between a majority of the electrode elements in the first set and a majority of the electrode elements in the second set in order to induce an electric field in the target region.

In some instances of the fourth method, the plan comprises generating a recommendation to move at least one set of electrode elements to a different position on the subject's body prior to the start of the treatment.

In some instances of the fourth method, the plan comprises selecting a first plurality of electrode elements from the first set and selecting a second plurality of electrode elements from the second set. Optionally, these instances may further comprise, subsequent to the step of generating the plan, applying an alternating voltage between the first plurality of electrode elements and the second plurality of electrode elements in order to induce an electric field in the target region.

Some instances of the fourth method further comprise, prior to the step of generating the plan, (a) obtaining an MRI and (b) registering the first tomographic image to the MRI, wherein the plan is also based on the MRI.

In some instances of the fourth method, each set of electrode elements includes at least 9 electrode elements and the first tomographic image includes at least 64 voxels.

Some instances of the fourth method further comprise obtaining a baseline MRI of the target region at a baseline time that is prior to the first window of time; generating, based on baseline impedance or conductance measurements obtained within 30 days of the baseline time, a baseline tomographic image of the target region; and registering the baseline tomographic image to the baseline MRI. The plan for treating the target region with alternating electric fields is further based on a comparison between the first tomographic image and the baseline tomographic image.

Some instances of the fourth method further comprise positioning a third set of at least 4 electrode elements on or in the subject's body on a third side of the target region; positioning a fourth set of at least 4 electrode elements on or in the subject's body on a fourth side of the target region, wherein the fourth side is opposite to the third side; applying a second plurality of electrical signals to the electrode elements in the third set and the electrode elements in the fourth set; and determining a second plurality of electrical characteristics of the target region while the second plurality of electrical signals is being applied. The first tomographic image of the target region is also based on the determined second plurality of electrical characteristics.

Some instances of the fourth method further comprise positioning a third set of at least 4 electrode elements on or in the subject's body on a third side of the target region; positioning a fourth set of at least 4 electrode elements on or in the subject's body on a fourth side of the target region, wherein the fourth side is opposite to the third side; applying a second plurality of electrical signals to the electrode elements in the third set and the electrode elements in the fourth set; and determining a second plurality of electrical characteristics of the target region while the second plurality of electrical signals is being applied. The first tomographic image of the target region is also based on the determined second plurality of electrical characteristics. These instances further comprise, subsequent to the step of generating the plan, (a) applying an alternating voltage between a majority of the electrode elements in the first set and a majority of the electrode elements in the second set in order to induce an electric field in the target region and (b) applying an alternating voltage between a majority of the electrode elements in the third set and a majority of the electrode elements in the fourth set in order to induce an electric field in the target region. Optionally, in these instances, each of the sets of electrode elements includes at least 9 electrode elements and the first tomographic image includes at least 64 voxels.

Another aspect of this application is directed to a first apparatus for generating an output specifying locations for one or more electrode arrays applying alternating electric fields to a target region in a subject's body using a first set of at least 4 electrode elements positioned on or in the subject's body on a first side of the target region and a second set of at least 4 electrode elements positioned on or in the subject's body on a second side of the target region that is opposite to the first side. The first apparatus comprises a processor programmed to: sequentially measure, during a first window of time, a respective first impedance or conductance between each of the electrode elements in the first set and each of the electrode elements in the second set; calculate, based on the first impedance or conductance measurements, a first impedance or conductance at each of at least 27 voxels that correspond to the target region; and generate a first output specifying locations for the electrode arrays, based on the first impedances or conductances of the voxels, for applying alternating electric fields to a first target in the target region.

In some embodiments of the first apparatus, the processor is further programmed to: input a baseline MRI of the target region at a baseline time that is prior to the first window of time; calculate, based on baseline impedance or conductance measurements obtained within 30 days of the baseline time, a baseline impedance or conductance at each of at least 27 voxels that correspond to the target region; and register the baseline impedances or conductances of the voxels to the baseline MRI. The first output specifying locations for the electrode arrays for applying alternating electric fields to the first target in the target region is further based on a comparison between the first impedances or conductances and the baseline impedances or conductances.

In some embodiments of the first apparatus, the processor is further programmed to: sequentially measure, during the first window of time and using a third set of at least 4 electrode elements positioned on or in the subject's body on a third side of the target region and a fourth set of at least 4 electrode elements positioned on or in the subject's body on a fourth side of the target region that is opposite to the third side, a respective first impedance or conductance between each of the electrode elements in the third set and each of the electrode elements in the fourth set; and calculate, based also on the measured impedances or conductances between the electrode elements in the third set and the electrode elements in the fourth set, the first impedance or conductance at each of the at least 27 voxels.

Optionally, in the embodiments of the previous paragraph, the processor may be further programmed to: sequentially re-measure, during a second window of time, at least a portion of said second window of time including time during which alternating electric fields are being applied to the target region, a respective second impedance or conductance between each of the electrode elements in the first set and each of the electrode elements in the second set, and between each of the electrode elements in the third set and each of the electrode elements in the fourth set; re-calculate, based on the impedance or conductance measurements, a second impedance or conductance at each of the at least 27 voxels that correspond to the target region; calculate a difference between the second impedance or conductance and the first impedance or conductance at each of the at least 27 voxels that correspond to the target region; and generate a second output specifying modified locations for one or more of the electrode arrays, based on the difference between the second impedance or conductance and the first impedance or conductance at each of the at least 27 voxels, for applying alternating electric fields to a new target in the target region.

Another aspect of this application is directed to a second apparatus for generating an output specifying locations for one or more electrode arrays applying alternating electric fields to a target region in a subject's body using a first set of at least 4 electrode elements positioned on or in the subject's body on a first side of the target region and a second set of at least 4 electrode elements positioned on or in the subject's body on a second side of the target region, wherein the second side is opposite to the first side. The second apparatus comprises, a processor programmed to: apply, during a first window of time, a first plurality of electrical signals to the electrode elements in the first set and the electrode elements in the second set; determine a first plurality of electrical characteristics of the target region while the first plurality of electrical signals is being applied; generate a first tomographic image of the target region based on the determined first plurality of electrical characteristics; and generate an output specifying locations for the electrode arrays, based on the first tomographic image, for applying alternating electric fields to the target region.

In some embodiments of the second apparatus, the processor is further programmed to: input a baseline MRI of the target region at a baseline time that is prior to the first window of time; generate, based on baseline impedance or conductance measurements obtained within 30 days of the baseline time, a baseline tomographic image of the target region; and register the baseline tomographic image to the baseline MRI. The output specifying locations for the electrode arrays for applying alternating electric fields to the target region is further based on a comparison between the first tomographic image and the baseline tomographic image.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

The embodiments described herein rely on actual measurements of electrical characteristics (e.g., impedances) obtained from the actual subject that is being treated (or will be treated) with TTFields. This approach can provide a significant improvement with respect to the prior art approach described above that uses conductivity values obtained from the scientific literature.

FIGS. 1A-1D depict four transducer arrays 50A/50P/50L/50R (where A, P, L, and R stand for anterior, posterior, left, and right, respectively) that are placed on the subject's skin in close proximity to a tumor (e.g., on the head for a person with glioblastoma). The transducer arrays 50 are arranged in two pairs, and each transducer array is connected via a multi-wire cable to an AC signal generator.

Figure 1A:
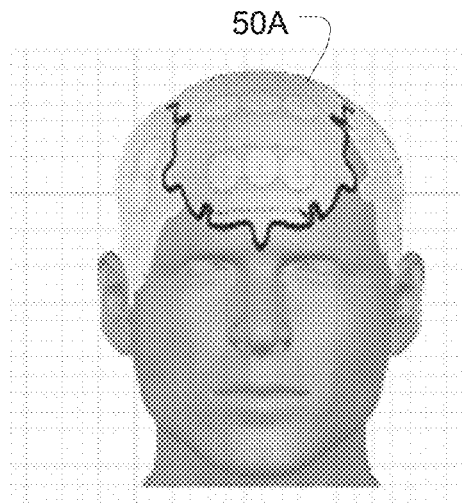
FIGS. 1A-1D depict four transducer arrays that are used to apply TTFields to a subject's body.
Figure 1B:
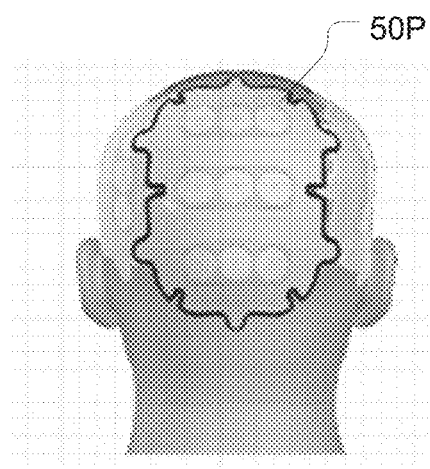
Figure 1C:
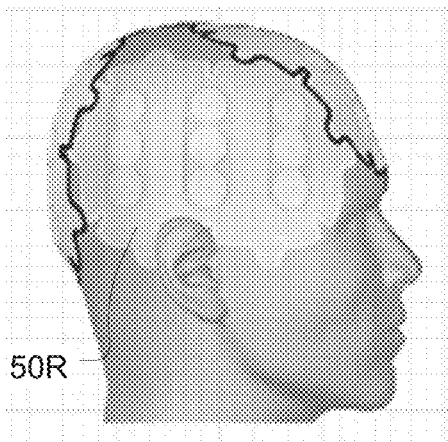
Figure 1D:
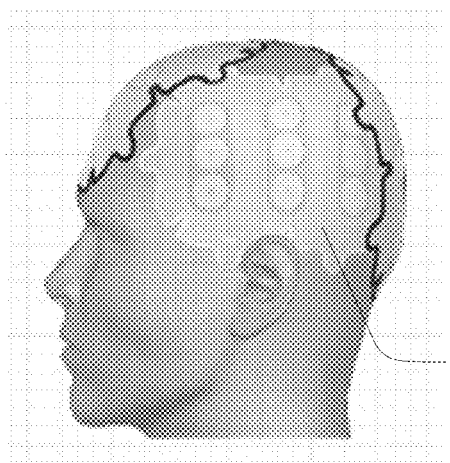
Figure 2:
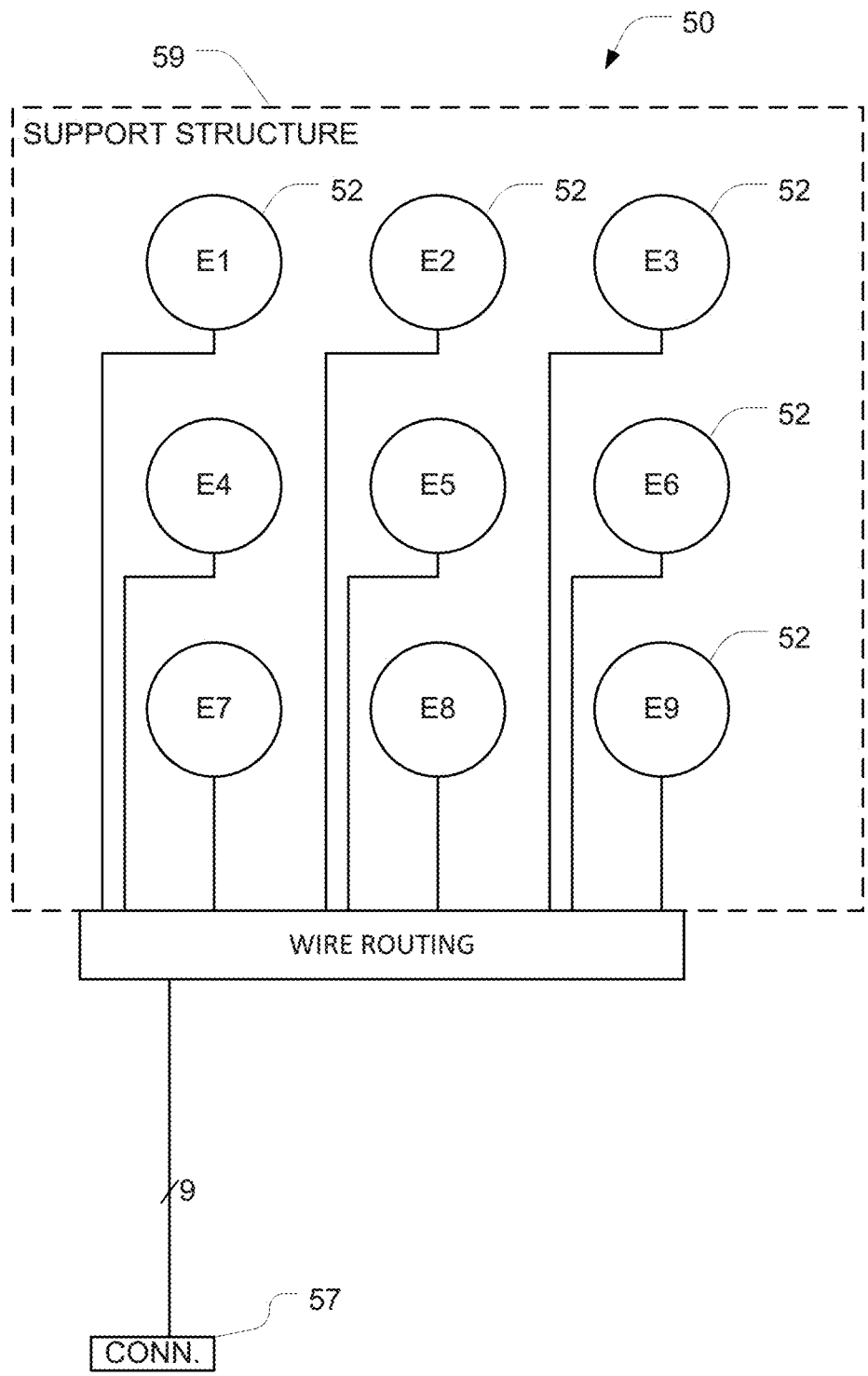
FIG. 2 depicts one approach for implementing each of the transducer arrays depicted in FIG. 1.

FIG. 2 depicts one approach for implementing each of the arrays 50A, 50P, 50L, and 50R depicted in FIGS. 1A-1D. Unlike the prior art configuration, (in which all of the electrode elements within any given transducer array are wired in parallel), this FIG. 2 embodiment provides an individual conductor for each of the electrode elements 52 in each of the transducer arrays 50, and this individual conductor terminates at a connector 57. This makes it possible to independently switch the current on and off for any given individual electrode element 52 in any one of the arrays 50. Note that while FIG. 2 depicts nine electrode elements 52 within any given transducer array 50, the number of electrode elements may vary (e.g., between 4 and 50).

Each transducer array 50 includes a at least four electrode elements 52, which are labeled E1-E9 in the FIG. 2 example. In some embodiments, each of these electrode elements 52 is implemented using an electrically conductive substrate (e.g., a round metal substrate) with a dielectric layer disposed thereon. In some preferred embodiments, each of these electrode elements 52 is a disc-shaped capacitively coupled electrode element (e.g., with a 2 cm diameter) that is similar to the prior art electrode elements used in the Optune® system, and the dielectric layer comprises a thin layer of ceramic material with a very high dielectric constant (e.g., >200). In other preferred embodiments, each of the electrode elements is implemented using a conductive pad on a flex circuit, and the dielectric layer comprises a thin layer of a polymer with a high dielectric constant (e.g., >10). In some preferred embodiments, the electrical connection to each of the electrode elements 52 comprises one or more traces on a flex circuit and/or one or more conductive wires.

In some preferred embodiments, each electrode element 52 is sandwiched between a layer of an electrically conductive medical gel (on the side that faces the subject) and a support structure 59. The support structure 59 holds the entire array 50 in place on the subject (e.g., using an adhesive) against the subject's body so that the dielectric layer of the electrode elements 52 faces the subject's body and can be positioned in contact with the subject's body. Optionally, this support structure 59 may comprise a flexible backing (e.g., a layer of foam material). Preferably, a layer of hydrogel is disposed between the dielectric layer of the electrode elements 52 and the subject's body when the transducer array 50 is placed against the subject's body. Construction of the support structure 59 may be implemented using any of a variety of conventional approaches that will be apparent to persons skilled in the relevant arts, including but not limited to self-adhesive fabric, foam, or plastic sheeting.

The connector 57 has a at least four pins. In the illustrated embodiment, the number of pins is the same as the number of electrode elements 52, and each of the first pins corresponds to a respective one of those electrode elements 52. Note that as used herein, the term "pin" can refer to either a male or female pin of the connector 57. Each transducer array 50 also has a plurality of conductors, and the number of these first conductors will depend on the number of electrode elements 52. Each of these conductors provides an electrically conductive path between the conductive substrate of one of the electrode elements 52 and a respective one of the pins in the connector 57. Each of these conductors may be implemented, for example, using a plurality of segments of wire and/or a plurality of traces on a flex circuit.

Because the connector 57 has an individual pin that corresponds to each of the individual electrode elements 52, the system that mates with the connector 57 can selectively energize or not energize each of the electrode elements 52 individually by either applying or not applying a signal to the respective pin on the connector 57.

Figure 3:
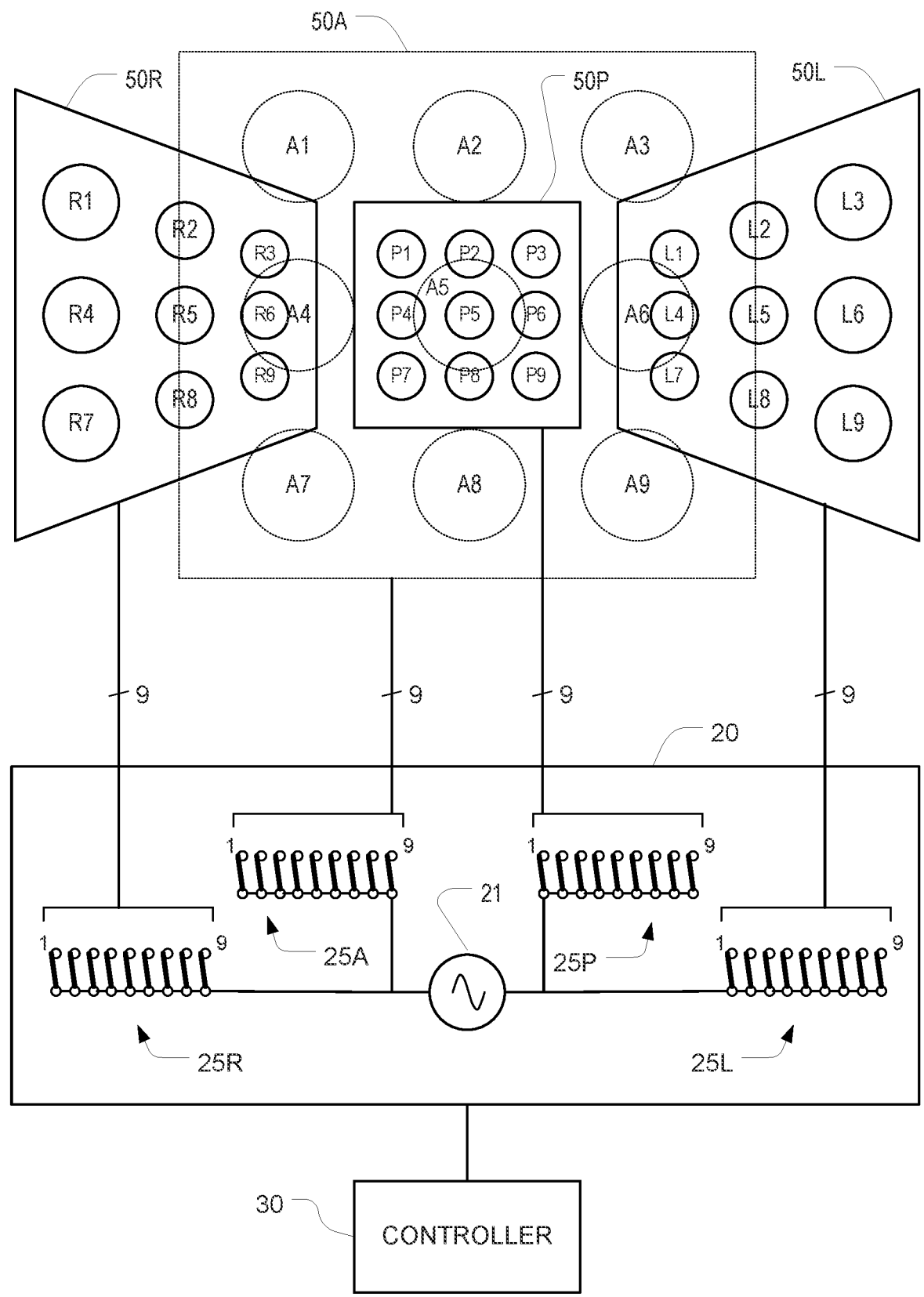
FIG. 3 is a block diagram of a system that uses four transducer arrays to apply TTFields to a subject's body.

FIG. 3 is a block diagram of a system that uses four copies of the transducer array 50 (described above in connection with FIG. 2) to apply TTFields to a subject. These four copies 50A/50P/50L/50R are positioned on the subject's body (e.g., placed on the subject's skin) anterior, posterior, to the left, and to the right of a tumor, respectively.

The system includes an AC voltage generator 21 that generates an AC voltage between its two output terminals. One phase of the AC voltage generator's output is provided to banks of switches 25A and 25R; and the other phase of the AC voltage generator's output is provided to banks of switches 25P and 25L. In the illustrated embodiment, each bank of switches includes nine individual switches, each of which corresponds to a respective element on one of the transducer arrays 50A/50P/50L/50R. The number of switches in each bank corresponds to the number of electrode elements in each array. So, for example, in embodiments that have four electrode elements in each array, each bank will include four switches.

The switches in banks 25R and 25A are arranged to, depending on the state of each individual switch, pass or block the first phase of the AC voltage generator's output to a corresponding element on the transducer arrays 50R and 50A. And the switches in banks 25P and 25L are arranged to, depending on the state of each individual switch, pass or block the other phase of the AC voltage generator's output to a corresponding element on the transducer arrays 50P and 50L.

The controller 30 controls the state of each switch within each of the banks 25A/25P/25L/25R by issuing appropriate control signals to the banks of switches. For example, the controller 30 could output 36 control bits, with one bit corresponding to each of the switches, such that when the control bit for any given switch is a 1, the switch will close, and when the control bit for any given switch is a 0, the switch will open.

Figure 4A:
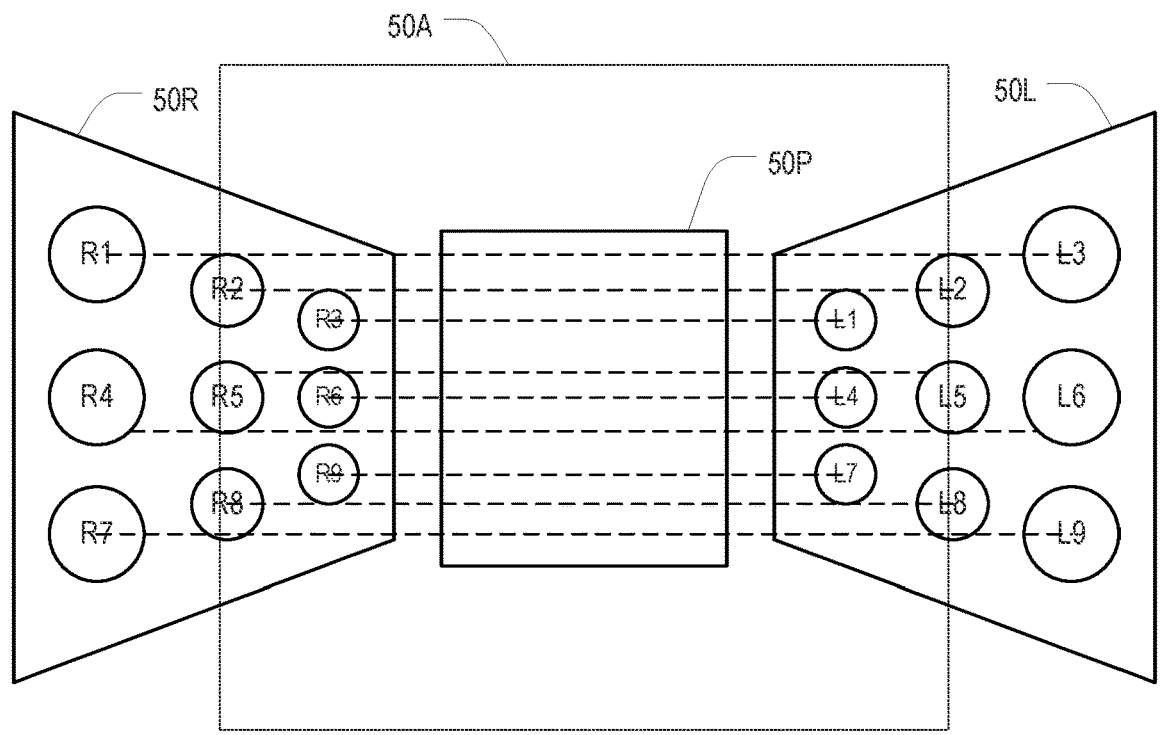
FIG. 4A depicts a situation in which TTFields are being applied between the right and left transducer arrays depicted in FIG. 3.
Figure 4B:
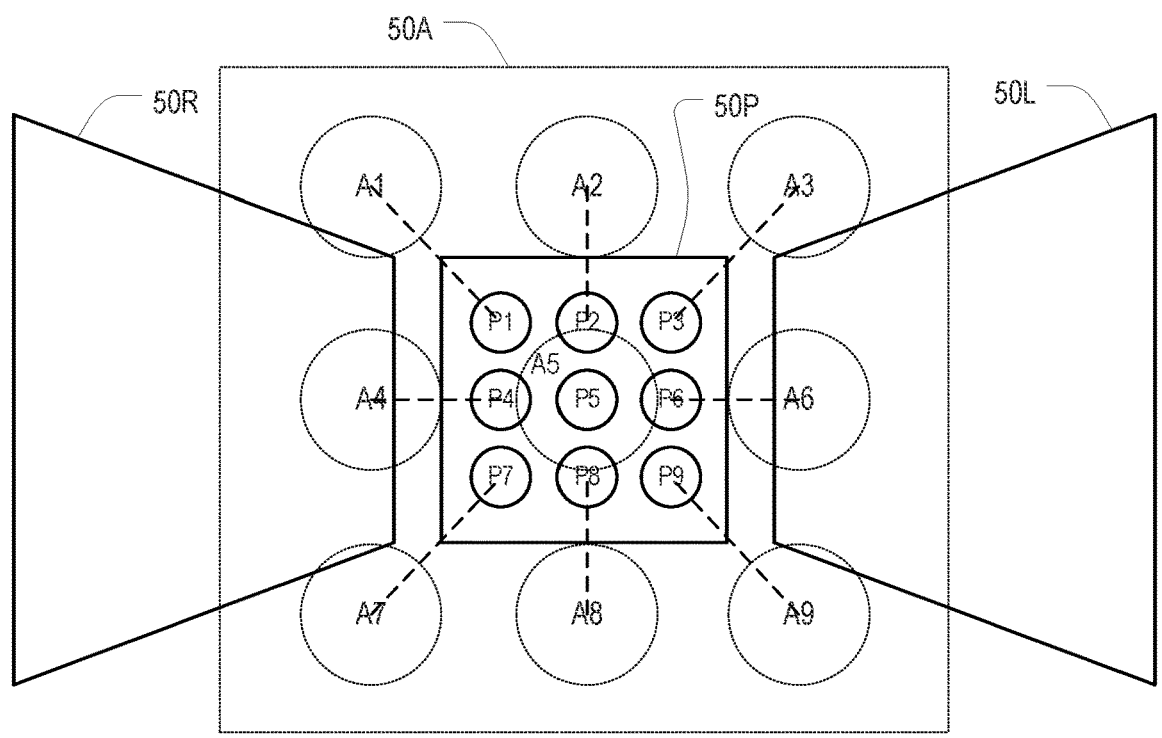
FIG. 4B depicts a situation in which TTFields are being applied between the anterior and posterior transducer arrays depicted in FIG. 3.

With this arrangement, when the controller 30 issues control signals to close all nine switches in bank 25R and to close all nine switches in bank 25L, one phase of the AC voltage generator's 21 output will be routed to all of the electrode elements R1-R9 in the first transducer array 50R, and the other phase of the AC voltage generator's output will be routed to all of the electrode elements L1-L9 in the second transducer array 50L. Because the arrays 50L and 50R are positioned on the subject's skin to the left and to the right of the tumor, respectively, the AC voltage on those transducer arrays 50L and 50R will induce an electric field through the subject's body, and the field lines of this electric field will run generally from right to left and left to right, as depicted schematically by the dashed lines in FIG. 4A. Note that in reality, the electric field lines will not be straight. But straight dashed lines are nevertheless used in FIGS. 4A-5D to represent the general direction of the field lines.

Similarly, when the controller 30 issues control signals to close all nine switches in bank 25A and to close all nine switches in bank 25P, one phase of the AC voltage generator's 21 output will be routed to all of the electrode elements A1-A9 in the third transducer array 50A, and the other phase of the AC voltage generator's output will be routed to all of the electrode elements P1-P9 in the fourth transducer array 50P. Because the arrays 50A and 50P are positioned on the subject's skin anterior and posterior with respect to the tumor, respectively, the AC voltage on those transducer arrays 50A and 50P will induce an electric field through the subject's body, and the field lines of this electric field will run generally from front to back and back to front, as depicted schematically by the dashed lines in FIG. 4B.

By periodically switching (e.g., every 1 second) back and forth between the two states described in the preceding paragraphs (i.e., one state in which all switches in banks 25R and 25L are closed, and another state in which all switches in banks 25A and 25P are closed), the controller causes the system to induce an electric field through the tumor that switches direction every 1 second. And the electric fields resulting from this control sequence will be equivalent to the electric fields that are induced in a subject's body using the prior art Optune® system (in which all of the electrode elements in any given transducer array are wired together in parallel), and can therefore be used to treat a tumor in the target volume.

Notably, in addition to replicating the sequence of electric fields that is provided by the prior art Optune® system, the FIG. 3 embodiment provides an important additional capability. This is because the very same hardware that induces the TTFields in the subject's body (as described above) can also be used to perform impedance tomography of the portion of the subject's body that lies between the transducer arrays 50A/50P/50L/50R. In alternative embodiments, separate sets of electrode elements are used for applying the TTFields and for performing the impedance tomography. When separate sets of electrode elements are used for these two functions, those separate sets of electrode elements match each other in some embodiments. Optionally, the set of electrode elements that is used for making impedance tomography measurements may be integrated into a snug-fitting cap, vest, or other garment.

Figure 5A:
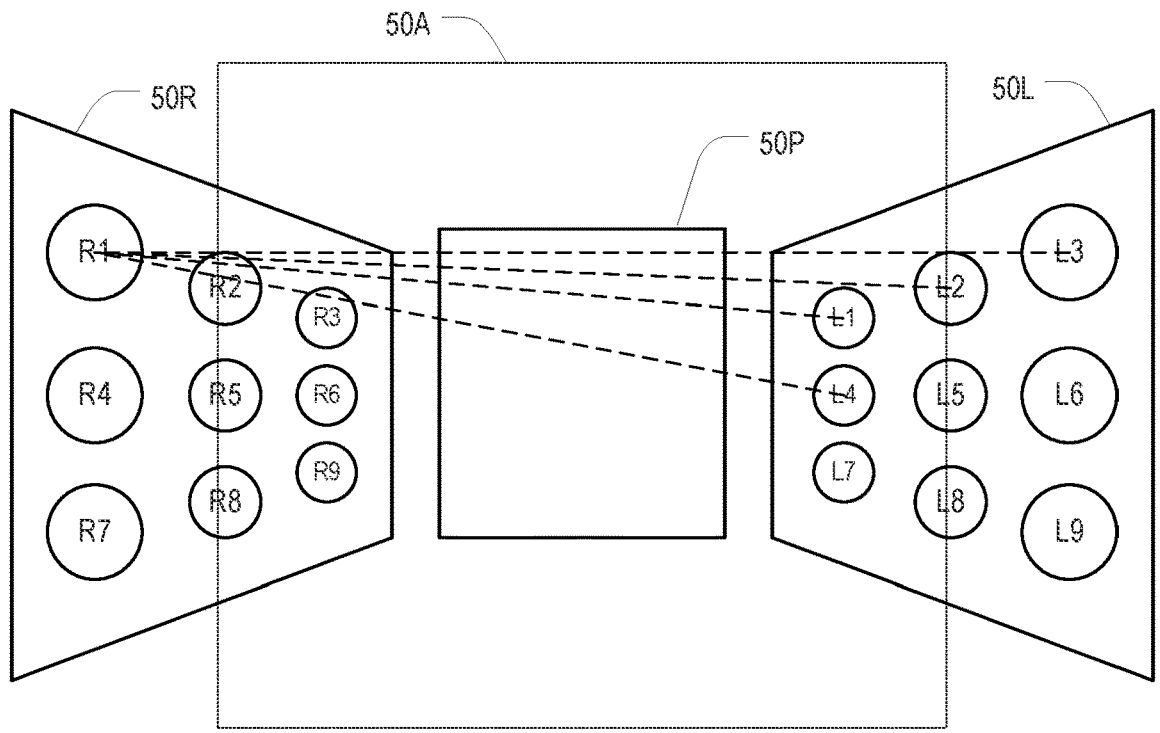
FIG. 5A is a schematic representation of impedance measurements being made between individual elements of the right transducer array and individual elements of the left transducer array.

More specifically, if the controller 30 closes a single switch selected from bank 25R and also closes a single switch selected from bank 25L, the output of the AC voltage generator 21 will be imposed between a single electrode element 52 from the first array 50R and a single electrode element 52 from the second array 50L. By measuring the voltage and current of the AC voltage generator 21, the impedance of the path that includes the two selected electrode elements can be determined. Referring now to FIG. 5A, if the controller 30 closes switch #1 in the first bank 50R and also closes switch #1 in the second bank 50L, and measures the voltage and current of the AC voltage generator 21, the impedance of the path that includes elements R1 and L1 (represented schematically by the dashed line between those two elements) can be determined. Similarly, if the controller 30 closes switch #1 in the first bank 50R and also closes switch #2 in the second bank 50L, and measures the voltage and current of the AC voltage generator 21, the impedance of the path that includes those elements R1 and L2 (represented schematically by the dashed line between those two elements) can be determined. Note that FIG. 5A only depicts four paths (using dashed lines) for clarity. But when the left array and the right array each include 9 elements, a total of 9×9=81 paths/combinations exist. Preferably, the controller 30 sequentially closes a single switch in the first bank 50R and a single switch in the second bank 50L corresponding to each of those 81 combinations, measures the voltage and current of the AC voltage generator 21 for each combination, and determines the impedance of the circuit that includes each of those 81 paths based on the voltage and current measurements.

Figure 5B:
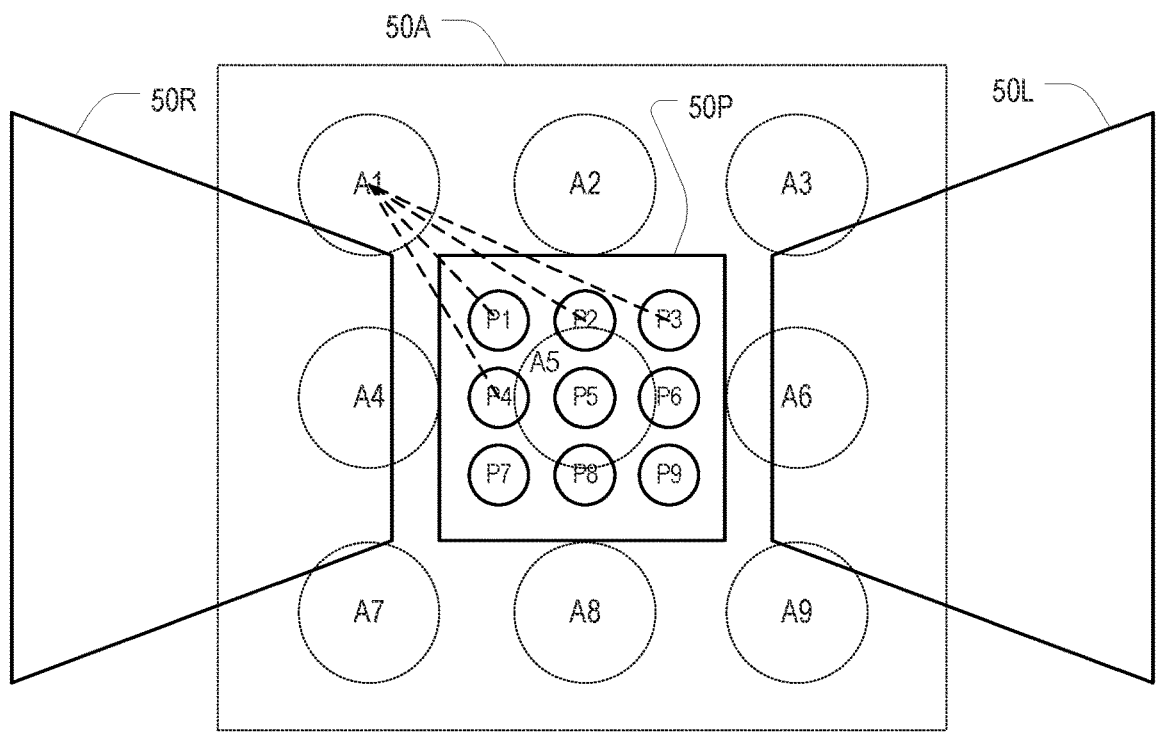
FIG. 5B is a schematic representation of impedance measurements being made between individual elements of the anterior transducer array and individual elements of the posterior transducer array.
Figure 5C:
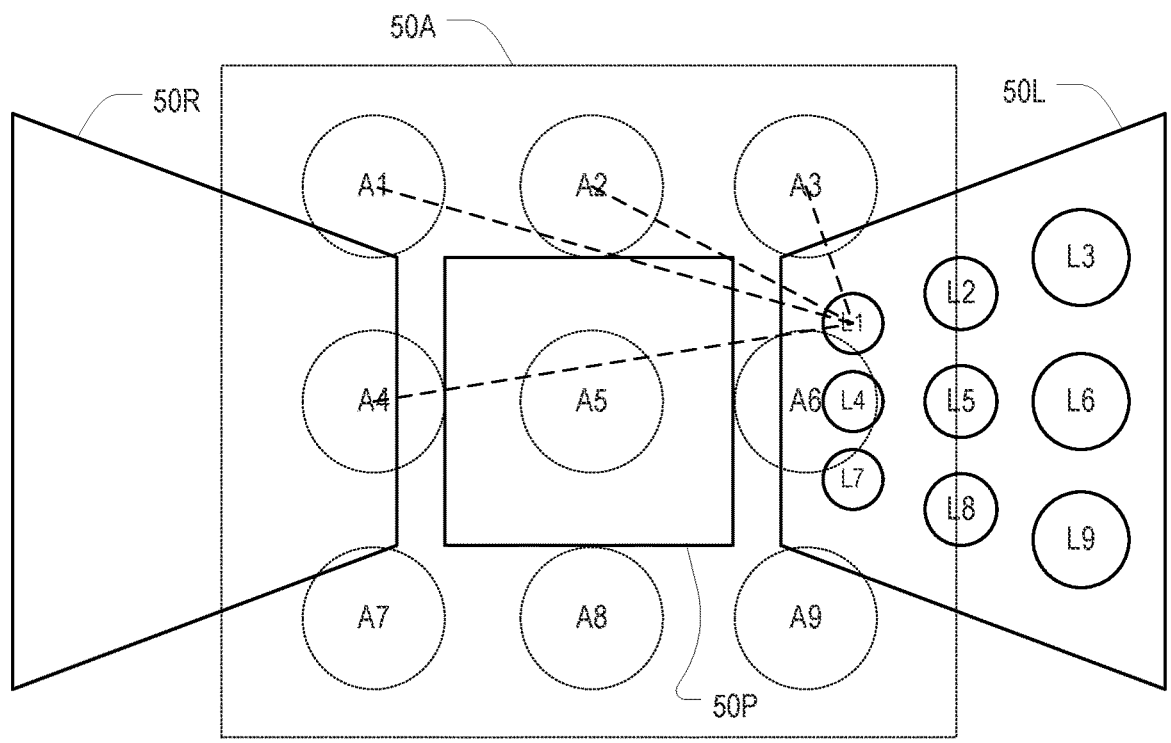
FIG. 5C is a schematic representation of impedance measurements being made between individual elements of the left transducer array and individual elements of the anterior transducer array.
Figure 5D:
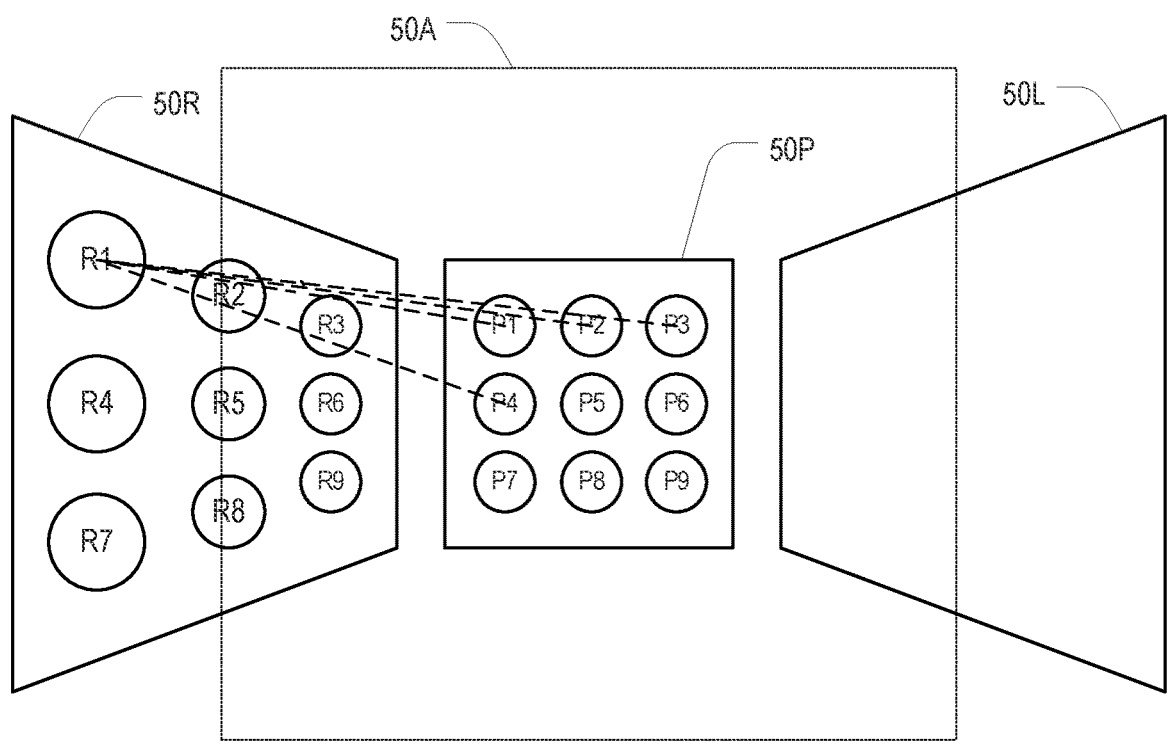
FIG. 5D is a schematic representation of impedance measurements being made between individual elements of the right transducer array and individual elements of the posterior transducer array.

Similarly, referring now to FIG. 5B, if the controller 30 closes switch #1 in the third bank 50A and also closes switch #1 in the fourth bank 50P, and measures the voltage and current of the AC voltage generator 21, the impedance of the path that includes elements A1 and P1 (represented schematically by the dashed line between those two elements) can be determined. Although only four paths are depicted (using dashed lines), when the anterior and posterior arrays each include 9 elements, a total of 9×9=81 paths/combinations exist. Preferably, the controller 30 sequentially closes a single switch in the third bank 50A and a single switch in the fourth bank 50P corresponding to each of those 81 combinations, and determine the impedance of the circuit that includes each of those 81 paths as described above in connection with FIG. 5A.

These 81+81=162 measurements are then fed into a conventional back propagation algorithm to determine the impedance at each voxel within a set of voxels that is positioned in the subject's body between the transducer arrays 50A/50P/50L/50R. (When the number of electrode elements in each array is greater than nine, the number of measurements will be larger; and when the number of electrode elements in each array is less than nine, the number of measurements will be smaller.) Notably, the resolution of these voxels need not be high, and relatively large voxels (e.g., voxels on the order of 1 cm$^3$) are suitable for the purposes described herein. In one example, a volume that measures 3 cm×3 cm×3 cm could be divided into a 3×3×3 array of voxels, which would mean that there are 27 voxels. Similarly, a volume that measures 4 cm×4 cm×4 cm could be divided into a 4×4×4 array of voxels, which would mean that there are 64 voxels.

Optionally, additional impedance measurements of the volume between the transducer arrays may be obtained and used to refine the calculation of the impedance at each voxel within the target volume. More specifically, referring now to FIG. 5C, if the controller 30 closes switch #1 in the second bank 50L and also closes switch #1 in the third bank 50A, and measures the voltage and current of the AC voltage generator 21, the impedance of the path that includes elements L1 and A1 (represented schematically by the dashed line between those two elements) can be determined. Although only four paths are depicted (using dashed lines), a total of 9×9=81 paths/combinations exist. So the controller 30 can sequentially close a single switch in the second bank 50L and a single switch in the third bank 50A corresponding to each of those 81 combinations, and determine the impedance of the circuit that includes each of those 81 paths as described above. Similarly, referring now to FIG. 5D, if the controller 30 closes switch #1 in the first bank 50R and also closes switch #1 in the fourth bank 50P, and measures the voltage and current of the AC voltage generator 21, the impedance of the path that includes elements R1 and P1 (represented schematically by the dashed line between those two elements) can be determined. Although only four paths are depicted (using dashed lines), a total of 9×9=81 paths/combinations exist. So the controller 30 can sequentially close a single switch in the first bank 50R and a single switch in the fourth bank 50P corresponding to each of those 81 combinations, and determine the impedance of the circuit that includes each of those 81 paths as described above in connection with FIG. 5A.

When the optional additional impedance measurements described in the previous paragraph are obtained, those impedance measurements are fed into the back propagation algorithm that determines the impedance at each voxel within the target volume to improve the accuracy of the resulting impedance tomography image.

When the impedance of each of the voxels in the region that lies between the transducer arrays is known, those impedances are used to make a model of the body part (e.g., the head). The electric field intensity (or power density) that is delivered to the tumor can then be calculated by applying model voltages to model electrodes that are positioned on the model of the body part, and calculating what the field intensity (or power density) will be within the tumor when a given AC voltage is applied to the model electrodes. And this information can be used to generate a plan for treating the target region with TTFields.

Notably, unlike the prior art techniques described in the background section, when the impedance at each voxel is generated using impedance tomography as described above, the result does not rely on assumptions about the electrical characteristics (e.g., conductivity) of the tissue between the electrodes. More specifically, because this technique uses impedance values for each voxel that are obtained by making measurements of the specific subject who is about to receive treatment using TTFields, this technique can provide improved accuracy with respect to the prior art techniques. Moreover, the techniques described herein that rely on actual impedance measurements advantageously eliminate cumbersome and computation-intensive finite element simulations.

Figure 6:
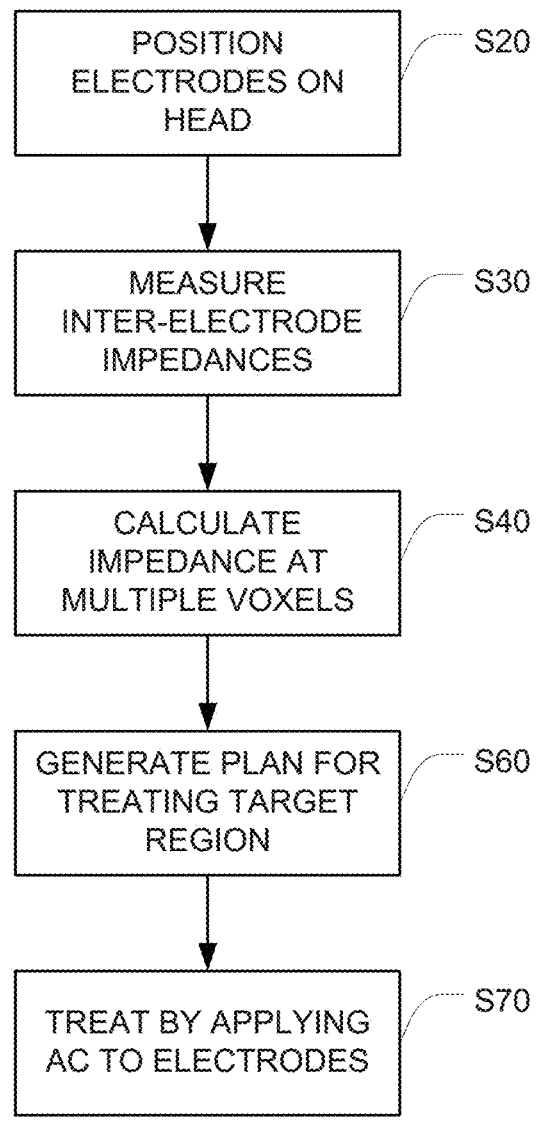
FIG. 6 depicts a method that uses a set of electrodes positioned on a subject's body to generate a plan for treating a target region in the subject's body using TTFields.

FIG. 6 depicts a method that uses a set of electrodes positioned on a subject's body to generate a plan for treating a target region in the subject's body using TTFields. Viewing FIG. 6 together with FIG. 3, in step S20 a first set 50R of N electrode elements is positioned on the subject's body on a first side (e.g., the right side) of the target region, and a second set 50L of M electrode elements is positioned on the subject's body on a second side (e.g., the left side) of the target region that is opposite to the first side. Both N and M are at least 4, and in the illustrated embodiment N=9 and M=9.

In step S30, the system sequentially measures, during a first window of time, a respective impedance between each of the N electrode elements in the first set 50R and each of the M electrode elements in the second set 50L. This may be accomplished, for example, by sequentially closing combinations of switches in the first bank 25R and the second bank 25L (as described above) so that an AC voltage is sequentially imposed between combinations of the electrode elements R1-R9 and L1-L9. While the AC voltage is imposed for each pair, the current and voltage is measured, and the impedance is calculated from those measurements. The first window of time should be long enough to obtain all necessary impedance measurements and will typically be less than 30 minutes (e.g., less than one minute).

Next, in step S40, the impedance at each of the voxels (e.g., at least 27 voxels or at least 64 voxels that correspond to the target region) within an impedance tomographic image is calculated (e.g., using a back propagation algorithm as described above). In step S60, a plan for treating the target region with TTFields is generated based on the calculated impedances of the voxels. The plan could include, for example, a recommendation of where to position the electrode elements (which are used to apply the TTFields) on the subject's body.

Although it is possible to implement the system that only positions electrode elements on first and second sides of the target region, improved results are obtained in embodiments that use optional additional sets of electrodes positioned on the subject's body. More specifically, as explained in connection with FIG. 3, a third set 50A of X electrode elements is positioned on the subject's body on a third side (e.g., anterior) of the target region, and a fourth set 50P of Y electrode elements is positioned on the subject's body on a fourth side (e.g., posterior) of the target region that is opposite to the third side. Both X and Y are at least 4, and in the illustrated embodiment X=9 and Y=9. The system sequentially measures, during the first window of time, a respective impedance between each of the X electrode elements in the third set 50A and each of the Y electrode elements in the fourth set 50P. The calculating of the impedance at each of the voxels in step S40 is also based on the measured impedances between the electrode elements in the third set and the electrode elements in the fourth set (in addition to the measured impedances between the electrode elements in the first set and the electrode elements in the second set).

Optionally, after the plan for treating the target region with alternating electric field is generated, an alternating voltage is applied between a majority (e.g., all) of the electrode elements R1-R9 in the first set 50R and a majority (e.g., all) of the electrode elements L1-L9 in the second set 50L in step S70 in order to induce an electric field in one direction in the target region, and an alternating voltage is applied between a majority (e.g., all) of the electrode elements A1-A9 in the third set 50A and a majority (e.g., all) of the electrode elements P1-P9 in the fourth set 50P in order to induce an electric field in another direction in the target region.

The plan for treating the target region with alternating electric fields may comprise generating a recommendation to move at least one set 50A/50P/50L/50R of electrode elements to a different position on the subject's body.

Figure 7:
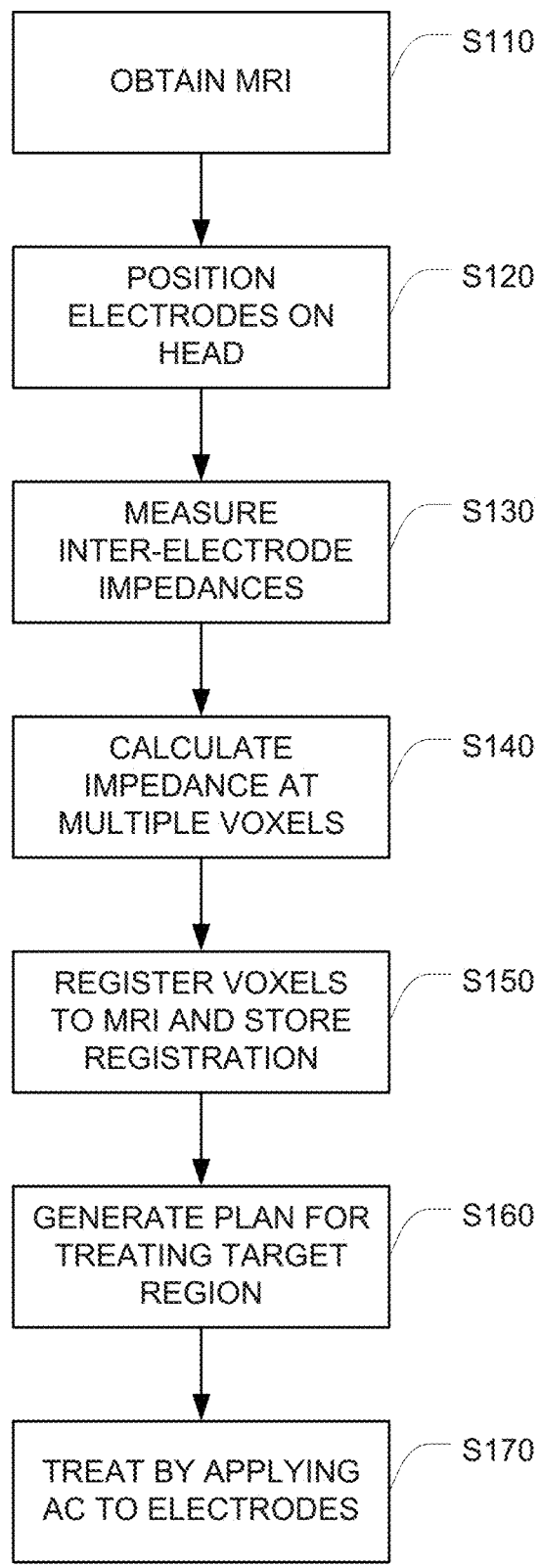
FIG. 7 depicts a method that uses both an MRI and a set of electrodes positioned on a subject's body to generate a plan for treating a target region in the subject's body using TTFields.

FIG. 7 depicts a method that uses both an MRI and a set of electrodes positioned on a subject's body to generate a plan for treating a target region in the subject's body using TTFields. First, in step S110, an MRI is obtained. Then, in steps S120-S140, an impedance tomographic image is obtained as described above in connection with S20-S40 in FIG. 6. The impedance tomographic image should be obtained within 30 days of the MRI, and more preferably within 7 days or within 1 day of the MRI, to facilitate registration of those two images. In step S150, the impedance tomography voxels are registered to the MRI (e.g., using a conventional image registration algorithm), and the registration is stored in memory. In this embodiment, the plan for treating the target region using TTFields may be generated in step S160 based on both the MRI and the impedance tomography image. The plan could include, for example, a recommendation of where to position the electrode elements (which are used to apply the TTFields) on the subject's body. Finally, treatment of the target region using TTFields occurs in step S170. The MRI obtained in step S110 and the impedance voxels obtained in step S140 serve as baselines for future comparisons.

Subsequent to the registration that occurs in step S150, changes in the tumor can be tracked using only impedance tomography images (e.g., obtained by repeating steps S20-S40 in FIG. 6) because if the tumor grows or shrinks, the impedance of voxels in the impedance tomography image will change. Thus, in some embodiments, the plan for treating the target region with alternating electric fields takes into account a comparison between the most recent impedances and the baseline impedances. For example, because tumors typically have different impedance than the tissue around it, a tumor can be detected by impedance tomography and changes in the tumor size can be tracked by impedance changes in the region of the tumor. For example, if the tumor impedance is higher that the tissue around it, an increase in the impedance of a voxel at the periphery of a tumor that was previously identified in the baseline MRI may be an indication that the portion of the tumor within that voxel has grown.

Based on any detected growth, shrinkage, or movement of the tumor, it may be desirable to reposition the electrode elements (which are used to apply the TTFields) to locations that provide increased field strength at the new location of the tumor. Determining the new location for the electrode elements may be implemented using conventional software for that purpose (e.g., Novotal™). Comparing the impedance tomography images to previous impedance tomography images may reduce the need for repeat MRIs or at least extend the interval of time between repeat MRIs.

Optionally, a new impedance tomography image may be generated at periodic intervals (e.g., by repeating steps S20-S40 in FIG. 6, e.g., once a day) or every time a new set of transducer arrays is positioned on the subject's body, and each new impedance tomography image is compared to one or more previous impedance tomography images (and optionally to the baseline MRI that was previously registered to the original impedance tomography image). Optionally, the conditions under which all of the impedance tomography images are obtained may be normalized to the extent possible (e.g., using new transducer arrays positioned on freshly shaved skin, normalizing the temperature and humidity at the time the impedance tomography images are captured, and/or normalizing the resting heart rate of the subject).

Optionally, whenever a new transducer array is positioned for the first time on the subject's body, an impedance tomography image is captured, and that impedance tomography image is compared to a previous impedance tomography image. This comparison can determine whether the new transducer array has been positioned in the same location on the subject's skin, or whether the new transducer array has been positioned at an offset location. In the latter situation, the system could output instructions that ask the subject (or a practitioner) to move one of the new transducer arrays to a new location (e.g., "move the right transducer array up 1 cm").

Note that while the embodiments above describe obtaining impedance measurements, similar results can be reached by replacing impedance measurements with conductance measurements. The nature of the changes required to switch from impedances to conductances will be apparent to persons skilled in the relevant arts.

Note also that while the embodiments above describe obtaining impedance measurements using transducer arrays positioned on the subject's body, the impedance measurements could also be obtained using transducer arrays positioned in the subject's body (e.g., by implanting the transducer arrays beneath the subject's skin).

Referring now to FIG. 3 taken alone, temperature sensors (e.g., thermistors, not shown) may optionally be incorporated into the array 50 to measure the temperature of the electrode elements; and hardware for sensing the temperature at each electrode element may be incorporated into the system.

Embodiments illustrated under any heading or in any portion of the disclosure may be combined with embodiments illustrated under the same or any other heading or other portion of the disclosure unless otherwise indicated herein or otherwise clearly contradicted by context.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of planning treatment of a target region in a subject's body using alternating electric fields, the method comprising:
   positioning a first set of N electrode elements on or in the subject's body on a first side of the target region, wherein N is at least 4;
   positioning a second set of M electrode elements on or in the subject's body on a second side of the target region, wherein M is at least 4 and wherein the second side is opposite to the first side;
   sequentially measuring, during a first window of time, a respective impedance or conductance between each of the N electrode elements in the first set and each of the M electrode elements in the second set;
   calculating, based on the impedance or conductance measurements, a first impedance or conductance at each of at least 27 voxels that correspond to the target region; and
   generating a plan, based on the first impedances or conductances of the voxels, for treating the target region with alternating electric fields.

2. The method of claim 1, further comprising:
   positioning a third set of X electrode elements on or in the subject's body on a third side of the target region, wherein X is at least 4;
   positioning a fourth set of Y electrode elements on or in the subject's body on a fourth side of the target region, wherein Y is at least 4 and wherein the fourth side is opposite to the third side; and
   sequentially measuring, during the first window of time, a respective impedance or conductance between each of the X electrode elements in the third set and each of the Y electrode elements in the fourth set,
   wherein the calculating of the first impedance or conductance at each of the at least 27 voxels is also based on the measured impedances or conductances between the electrode elements in the third set and the electrode elements in the fourth set.

3. The method of claim 2 further comprising, subsequent to the step of generating the plan, (a) applying an alternating voltage between a majority of the electrode elements in the first set and a majority of the electrode elements in the second set in order to induce an electric field in the target region, and (b) applying an alternating voltage between a majority of the electrode elements in the third set and a majority of the electrode elements in the fourth set in order to induce an electric field in the target region.

4. The method of claim 2, wherein the plan comprises generating a recommendation to move at least one set of electrode elements to a different position on or in the subject's body.

5. The method of claim 4 further comprising, prior to the step of generating the plan, (a) obtaining an MRI and (b) registering the voxels to the MRI, wherein the recommendation to move at least one set of electrode elements to a different position is also based on the MRI.

6. The method of claim 2, wherein N is at least 9, M is at least 9, X is at least 9, and Y is at least 9.

7. The method of claim 1, further comprising
   obtaining a baseline MRI of the target region at a baseline time that is prior to the first window of time;
   calculating, based on baseline impedance or conductance measurements obtained within 30 days of the baseline time, a baseline impedance or conductance at each of at least 27 voxels that correspond to the target region; and
   registering the baseline impedances or conductances of the voxels to the baseline MRI, wherein the plan for treating the target region with alternating electric fields is further based on a comparison between the first impedances or conductances and the baseline impedances or conductances.

8. A method of planning treatment of a target region in a subject's body using alternating electric fields, the method comprising:
determining, based on a plurality of impedance or conductance measurements obtained during a first window of time, a first impedance or conductance at each of at least 27 voxels that correspond to the target region; and
generating a plan for treating the target region with alternating electric fields, based on the first impedances or conductances of the voxels.

9. The method of claim 8, wherein the plurality of impedance or conductance measurements are obtained by positioning at least 10 electrode elements on or in the subject's body and applying a plurality of electrical signals to the electrode elements.

10. The method of claim 8, further comprising treating a tumor in the target region by applying an alternating voltage between a plurality of the electrode elements in order to induce an electric field in the target region.

11. The method of claim 8, further comprising
obtaining a baseline MRI of the target region at a baseline time that is prior to the first window of time;
calculating, based on baseline impedance or conductance measurements obtained within 30 days of the baseline time, a baseline impedance or conductance at each of at least 27 voxels that correspond to the target region; and
registering the baseline impedances or conductances of the voxels to the baseline MRI,
wherein the plan for treating the target region with alternating electric fields is further based on a comparison between the first impedances or conductances and the baseline impedances or conductances.

12. A method of adaptively treating a cancer patient by administering alternating electric fields to a target region in a patient's body combined with in-situ measurement of cancer progression or regression or redistribution in the target region, the method comprising:
positioning a first set of N electrode elements on or in the patient's body on a first side of the target region, wherein N is at least 4;
positioning a second set of M electrode elements on or in the patient's body on a second side of the target region, wherein M is at least 4 and wherein the second side is opposite to the first side;
sequentially applying, during a first period of time, a plurality of electrical signals to the electrode elements in the first set and the electrode elements in the second set;
determining, based on the applied electrical signals, a first impedance or conductance at each of at least 27 voxels that correspond to the target region;
determining a first target location of at least one first target selected from cancer targets:
(i) tumor(s) or residual tumor(s)
(ii) cancer cell cluster(s)
(iii) cancer cell(s)
(iv) boundary region of cancer cells and healthy tissue;
delivering alternating electric fields treatment to the first target at the first target location in the patient's body;
monitoring changes over a second period of time in the electrical impedance or conductance of the voxels, using electrical impedance or conductance measurements, at least a portion of said second period of time includes time during which the patient is receiving alternating electric fields treatment; and
administering alternating electric fields to at least one second target in the target region, using a modified electric field intensity or a modified positioning, or both, for at least one set of electrode elements in response to observed changes in the electrical impedance or conductance of the voxels; and, optionally, repeating, one or more times, one or more steps.

13. The method of claim 12, further comprising:
positioning a third set of X electrode elements on or in the patient's body on a third side of the target region, wherein X is at least 4;
positioning a fourth set of Y electrode elements on or in the patient's body on a fourth side of the target region, wherein Y is at least 4 and wherein the fourth side is opposite to the third side; and
sequentially applying, during the first period of time, a plurality of electrical signals to the electrode elements in the third set and the electrode elements in the fourth set,
wherein the determining of the first impedance or conductance at each of the at least 27 voxels is also based on the plurality of electrical signals applied to the electrode elements in the third set and the electrode elements in the fourth set.

14. The method of claim 13, wherein the step of delivering alternating electric fields treatment to the first target at the first target location in the patient's body comprises (a) applying an alternating voltage between a majority of the electrode elements in the first set and a majority of the electrode elements in the second set in order to induce an electric field in the target region, and (b) applying an alternating voltage between a majority of the electrode elements in the third set and a majority of the electrode elements in the fourth set in order to induce an electric field in the target region.

15. The method of claim 13, wherein N is at least 9, M is at least 9, X is at least 9, and Y is at least 9.

16. The method of claim 12 further comprising, prior to the step of determining a first target location of at least one first target and prior to delivering alternating electric fields treatment to the first target, generating a baseline tomographic image of the target region based on the first impedance or conductance at each of the voxels that correspond to the target region.

17. The method of claim 16 further comprising, prior to the step of determining a first target location of at least one first target and prior to delivering alternating electric fields treatment to the first target, (a) obtaining a baseline MRI of the target region and (b) registering the first impedances or conductances at each of the voxels to the baseline MRI or registering the baseline tomographic image of the target region based on the first impedance or conductance at each of the voxels to the baseline MRI, wherein determining the first target location of the at least one first target is also based on the baseline MRI.

18. The method of claim 12, wherein monitoring changes over a second period of time in the electrical impedance or conductance of the voxels is used to assess progression or regression of cancer occurring at the first target location, or growth of a new cancer away from the first target location.

19. The method of claim 12, wherein monitoring changes over a second period of time in the electrical impedance or conductance of the voxels, includes measuring electrical impedance or conductance of the voxels concurrently with administering alternating electric fields to the target region.

20. The method of claim 12, further comprising an iterative process of performing one or more steps of the method performed over a third period of time to identify one or more additional cancer targets at one or more new locations of growth of cancer away from the first target location and administering alternating electric fields to at least one of the additional cancer targets.

* * * * *